(12) United States Patent
Hendriks et al.

(10) Patent No.: US 7,053,051 B2
(45) Date of Patent: May 30, 2006

(54) METHODS OF PREPARING CROSSLINKED MATERIALS AND BIOPROSTHETIC DEVICES

(75) Inventors: Marc Hendriks, Brunssum (NL); Frank Everaerts, Maastricht (NL); Mirian Gillissen, Gulpen (NL); Michel Verhoeven, Maastricht (NL); Mark W. Torrianni, Suan Juan Capistrano, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/974,206

(22) Filed: Oct. 27, 2004

(65) Prior Publication Data

US 2005/0136510 A1    Jun. 23, 2005

Related U.S. Application Data

(60) Provisional application No. 60/514,881, filed on Oct. 28, 2003.

(51) Int. Cl.
*A61K 38/00* (2006.01)

(52) U.S. Cl. ...................................................... 514/12

(58) Field of Classification Search ................ 530/350; 514/12
See application file for complete search history.

(56) References Cited

U.S. PATENT DOCUMENTS

| | | | |
|---|---|---|---|
| 4,279,812 A | 7/1981 | Cioca | |
| 4,687,841 A | 8/1987 | Spilburg et al. | |
| 4,958,008 A | 9/1990 | Petite et al. | |
| 5,162,430 A | 11/1992 | Rhee et al. | |
| 5,264,551 A | 11/1993 | Petite et al. | |
| 5,306,782 A | 4/1994 | Chang et al. | |
| 5,374,539 A | 12/1994 | Nimni et al. | |
| 5,639,796 A | 6/1997 | Lee | |
| 5,674,725 A | 10/1997 | Beertsen et al. | |
| 5,733,994 A | 3/1998 | Koepff et al. | |
| 5,782,931 A * | 7/1998 | Yang et al. | 8/94.11 |
| 6,117,979 A | 9/2000 | Hendriks et al. | |
| 6,166,184 A * | 12/2000 | Hendriks et al. | 530/356 |
| 6,330,481 B1 | 12/2001 | Van Wijk et al. | |
| 6,385,491 B1 | 5/2002 | Lindemans et al. | |
| 2002/0022588 A1 | 2/2002 | Wilkie et al. | |
| 2002/0028243 A1 | 3/2002 | Masters | |
| 2002/0038004 A1 | 3/2002 | Stolowitz et al. | |
| 2002/0038150 A1 | 3/2002 | Urry | |

FOREIGN PATENT DOCUMENTS

| | | |
|---|---|---|
| EP | 0897942 A1 * | 8/1988 |
| EP | 0898973 A2 * | 8/1998 |
| EP | 1 172 399 A1 | 1/2002 |
| JP | 6-293870 | 10/1994 |
| JP | 7-316193 | 12/1995 |
| JP | 2002-80501 | 3/2002 |
| WO | WO 85/04413 A1 | 10/1985 |
| WO | WO 93/00935 A1 | 1/1993 |
| WO | WO 93/10231 A1 | 5/1993 |
| WO | WO 96/03093 A1 | 2/1996 |
| WO | WO 00/33888 A2 | 6/2000 |
| WO | WO 00/35372 A2 | 6/2000 |
| WO | WO 00/52052 A1 | 9/2000 |
| WO | WO 00/56885 A1 | 9/2000 |
| WO | WO 00/72872 A1 | 12/2000 |
| WO | WO 00/72893 A2 | 12/2000 |
| WO | WO 01/45761 A1 | 6/2001 |
| WO | WO 01/61353 A1 | 8/2001 |
| WO | WO 01/91821 A1 | 12/2001 |
| WO | WO 01/92322 A1 | 12/2001 |
| WO | WO 02/05959 A2 | 1/2002 |
| WO | WO 02/09647 A2 | 2/2002 |
| WO | WO 02/34306 A1 | 5/2002 |

OTHER PUBLICATIONS

Damnik et al., Biomaterials, (1996), v. 17(8), pp. 765-773.*
U.S. Appl. No. 60/514,881 filed Oct. 28, 2003, Hendriks et al.
Gratzer et al., "Control of pH Alters the Type of Crosslinking Produced by 1-Ethyl-3-(3-Dimethylaminopropyl)-Carbodiimide (EDC) Treatment of Acellular Matrix Vascular Grafts," *J. Biomed. Mat. Res.*, 2001;58:172-179.
Hafemann et al., "Crosslinking by 1-ethyl-3-(3-dimethylaminopropyl)-carbodiimide (EDC) of a collagen/elastin membrane meant to be used as a dermal substitute; effects on physical, biochemical and biological features in vitro," *J. Mat. Sci.: Mat. Med.*, 2001;12:437-446.
Heidemann et al., "Polycondensation of tripeptides by a one pot procedure," *Die Makromol. Chem.*, 1973;166:1-14 (English language summary).

(Continued)

Primary Examiner—Karen Cochrane Carlson
Assistant Examiner—Agnes Rooke
(74) *Attorney, Agent, or Firm*—Mueting, Raasch & Gebhardt, P.A.

(57) ABSTRACT

Methods for making crosslinked material, such as collagen-based material, and bioprosthetic devices. The crosslinked material includes hydroxyl groups, carboxyl groups, and amine groups prior to crosslinking. The methods include removing at least a portion of the zero-length ester crosslinks in a crosslinked material and/or blocking at least a portion of the amine groups that are reactive with carboxyl groups and form zero-length crosslinks.

60 Claims, 2 Drawing Sheets

OTHER PUBLICATIONS

Hypolite et al., "Formation of Microscale Gradients of Protein Using Heterobifunctional Photolinkers," *Bioconjugate Chem.*, 1997;8:658-663.

Katchalski, "Novel Techniques for the Synthesis of Linear and Cyclic Peptides," *Hypotensive Pept., Proc. Int. Symp.*, 1966; meeting date Oct. 25-29, 1965:55-62.

Kim et al., "Three-Dimensional Porous Collagen/Chitosan Complex Sponge for Tissue Engineering." *Fibers and Polymers*, 2001;2(2):64-70.

Kuijpers et al., "Characterization of the Network Structure of Carbodiimide Crosslinked Gelatin Gels," *Macromolecules*, 1999;32:3325-3333.

Kuroyanagi et al., "Preparation of graft polypeptide binding bleomycin derivative," *Int. J. Biol. Macromol.*, 1986;8:52-56.

Lee et al., "Crosslinking of tissue-derived biomaterials in 1-ethyl-3-(3-dimethylaminopropyl)-carbodiimide (EDC)," *J. Mat. Sci: Mat. Med.*, 1996;7:531-541.

Nishino et al., "Peptide Hydroxamic Acids as Inhibitors of Thermolysin," *Biochemistry*, 1978;17(14):2846-2850.

Olde Damink, "Cross-linking of dermal sheep collagen using a water-soluble carbodiimide," *Biomaterials*, 1996;17:765-773.

Olde Damink et al., "In vitro degration of dermal sheep collagen cross-linked using a water-soluble carbodiimide," *Biomaterials*, 1996;17:679-84.

Pieper et al., "Development of tailor-made collagen-glycosaminoglycan matrices: EDC/NHS crosslinking, and ultrastructural aspects," *Biomaterials*, 2000;21: 581-593.

Shibnev et al., "N-hydroxysuccinimide Esters in the Synthesis of Collagen-Type Structures," *Bulletin of the Academy of Sciences of the USSR (translation of Izv. Akad. Nauk SSSR, Ser. Khim.)*, 1969;11:2367-2370.

Shibnev et al., "Synthesis of Different Activated Esters of Monomeric Tripeptides in Order to Obtain a Model of the Collagen Structure," *Bulletin of the Academy of Sciences of the USSR (translation of Izv. Akad. Nauk SSSR, Ser. Khim.)*, 1969;11:2362-2366.

van Wachem et al., "Biocompatibility and tissue regenerating capacity of crosslinked dermal sheep collagen," *J. Biomed. Mat. Res.*, 1994;28:353-363.

van Wachem et al., "In vivo biocompatibility of carbodiimide-crosslinked collagen matrices: Effects of crosslink density, heparin immobilization, and bFGF loading," *J. Biomed. Mat. Res.*, 2001;55(3):368-378.

Wissink et al., "Improved endothelialization of vascular grafts by local release of growth factor from heparinized collagen matrices," *J. Control. Release*, 2000;64:103-114.

Wissink et al., "Endothelial cell seeding of (heparinized) collagen matrices: effects of bFGF pre-loading on proliferation (after low density seeding) and pro-coagulant factors," *J. Control Release*, 2000;67:141-155.

Wissink et al., "Binding and release of basic fibroblast growth factor from heparinized collagen matrices," *Biomaterials*, 2001;22:2291-2299.

Wissink et al., "Immobilization of heparin to EDC/NHS-crosslinked collagen. Characterization and in vitro evaluation," *Biomaterials*, 2001;22:151-163.

Zeeman et al., "Successive epoxy and carbodiimide crosslinking of dermal sheep collagen," *Biomaterials*, 1999;20:921-931.

Wissink et al., "Endothelial Cell Seeding on Crosslinked Collagen: Effects of Crosslinking on Endothelial Cell Proliferation and Functional Parameters," *Thrombosis and Haemostatis*, 2000;84:325-331.

\* cited by examiner

METHODS OF PREPARING CROSSLINKED MATERIALS AND BIOPROSTHETIC DEVICES

CROSS-REFERENCE TO RELATED APPLICATIONS

The present application claims the benefit of U.S. Provisional Application No. 60/514,881, filed on 28 Oct. 2003, which is incorporated herein by reference in its entirety.

BACKGROUND OF THE INVENTION

Prosthetic implants, which can be made from natural or synthetic materials, include, for example, heart valves, vascular grafts, urinary bladder prostheses, and tendon prostheses. Bioprostheses (i.e., prostheses derived from natural tissue) are typically preferred over synthetic or mechanical prostheses. For example, natural tissue valves are preferred over mechanical valves because tissue valves stimulate the natural flow of the blood better than mechanical valves. Also, no blood anticoagulants are needed when natural tissue valves are used.

Tissue heart valve prostheses are typically made from either porcine aortic valves or bovine pericardium; ostrich or kangaroo are successful alternatives. Such valves are typically made by pretreating the tissue with glutaraldehyde or other crosslinking agents, as discussed below, and sewing the tissue into a flexible metallic alloy or polymeric stent. Such animal tissues mainly consist of collagen and elastin. These components provide the tissues, particularly heart valves, with their needed mechanical strength and flexibility.

Collagen-based materials, including whole tissue, are finding increased use in the manufacture of biomedical devices, such as prosthetic implants. This is particularly true for heart valves. Collagen is the major structural protein in higher vertebrate organisms forming extracellular fibers or networks in practically every tissue of the body, including skin, bone, cartilage, and blood vessels. Its molecular structure is highly conserved across many species lines, which makes it an ideal implant material with good biocompatibility. In medical devices, collagen provides a more physiological, isotropic environment that has been shown to promote the growth and function of different cell types, facilitating the rapid overgrowth of host tissue after implantation.

Basically, three types of collagen-based materials can be identified, based on the differences in the purity and integrity of the collagen fiber bundle network initially present in the material. The first type includes whole tissue including non-collagenous substances or cells. As a result of using whole tissue, the naturally occurring composition and the native strength and structure of the collagen fiber bundle network are preserved. Whole tissue xenografts have been used in construction of heart valve prostheses, and also in vascular prostheses. However, the presence of soluble proteins, glycoproteins, glycosaminoglycans, and cellular components in such whole tissue xenografts may induce an immunological response of the host organism to the implant.

The second type of collagen-based material includes only the collagen matrix without the non-collagenous substances. The naturally occurring structure of the collagen fiber bundle network is thus preserved, but the antigenicity of the material is reduced. The fibrous collagen materials obtained by removing the antigenic non-collagenous substances will generally have suitable mechanical properties.

The third type of collagen-based material is purified fibrous collagen. Purified collagen is obtained from whole tissue by first dispersing or solubilizing the whole tissue by either mechanical or enzymatic action. The collagen dispersion or solution is then reconstituted by either air drying, lyophilizing, or precipitating out the collagen. A variety of geometrical shapes like sheets, tubes, sponges or fibers can be obtained from the collagen in this way. The resulting materials, however, do not have the mechanical strength of the naturally occurring fibrous collagen structure.

A major problem in the use of collagen-based materials, and especially whole tissue xenografts in which the donor and recipient are phylogenetically distant, for implantation is that these materials are prone to hyperacute rejection. This is a rapid and violent rejection reaction that leads to the destruction of the xenograft. Hyperacute rejection appears to be triggered by components of natural immunity, most notably natural antibodies and complement.

In order to use collagen-based materials in manufacturing medical devices, particularly bioprosthetic implants, their durability and in vivo performance typically need to be improved. This can be done by crosslinking the material. Crosslinking of collagen-based materials is used to suppress the antigenicity of the material in order to prevent the hyperacute rejection reaction. In addition, crosslinking is used to improve mechanical properties and enhance resistance to both mechanical and proteolytic degradation.

Several chemical crosslinking methods for collagen-based materials are known. These methods typically involve the reaction of a bifunctional reagent (i.e., a spacer) with the amine groups of lysine or hydroxylysine residues on different polypeptide chains or the activation of carboxyl groups of glutamic and aspartic acid residues followed by the reaction with an amine group of another polypeptide chain to give an amide bond. For example, glutaraldehyde (GA), which is a bifunctional aldehyde, or diisocyanates bridge amine groups on two adjacent polypeptide chains to form crosslinks.

Another method of crosslinking involves the formation of an acyl azide. The acyl azide method involves the activation of carboxyl groups in the polypeptide chain. The activated groups form crosslinks by reaction with collagen amine groups of another chain.

Also, water-soluble carbodiimides can be used to activate the free carboxyl groups of glutamic and aspartic acid moieties in collagen. Activation of the carboxyl groups with carbodiimides, such as 1-ethyl-3-(3-dimethylaminopropyl)carbodiimide.HCl (EDC), gives O-acylisourea groups. A condensation reaction by nucleophilic attack of a free amine group of a (hydroxy)lysine residue with urea as a leaving group results in formation of an amide crosslink. The O-acylisourea can also be hydrolyzed or rearranged to an N-acylurea, which is much more stable and will not react to form a crosslink. Addition of N-hydroxysuccinimide (NHS) prevents this rearrangement, however. In the presence of NHS, the O-acylisourea can be converted to an NHS activated carboxyl group, which also can react with a free amine group to form a crosslink.

U.S. Pat. No. 6,166,184 discloses a method for making a bioprosthetic device made of collagen-based material that includes: blocking at least a portion of the collagen amine groups with a blocking agent; activating at least a portion of the collagen carboxyl groups after blocking at least a portion of the collagen amine groups to form activated carboxyl groups; and contacting the activated collagen carboxyl groups with a polyfunctional spacer (preferably a bifunctional spacer) to crosslink the collagen-based material.

Although the resultant material has a generally high degree of crosslinking and a generally high resistance towards enzymatic digestion, and crosslinked material maintains a relatively high degree of flexibility without substantial stiffening over time, there is still a need for methods of crosslinking collagen-based materials that are even more flexible.

SUMMARY

The present invention provides methods for making crosslinked materials, particularly crosslinked collagen-based materials, and bioprosthetic devices (typically an implant or implantable device) that include collagen-based materials. The methods involve removing zero-length ester crosslinks in crosslinked materials that prior to crosslinking included amine groups, carboxyl groups, and hydroxyl groups, such as collagen-based material. Alternatively, or additionally, the methods involve blocking at least a portion of the amine groups prior to crosslinking.

Significantly, preferred methods of the present invention yield a material with a generally high degree of crosslinking and a generally high resistance toward enzymatic digestion, while the material maintains a relatively high degree of flexibility without substantial stiffening over time. Preferred materials are also preferably highly hydrophilic, which is believed to contribute to biocompatibility of the materials. The methods of the present invention are particularly suitable for crosslinking cardiovascular bioprostheses, such as heart valves and vascular grafts.

In one embodiment of the invention, a method for making a material includes: providing a crosslinked material having zero-length ester crosslinks and spacer crosslinks, wherein the material included amine groups, carboxyl groups, and hydroxyl groups prior to crosslinking; and removing at least a portion of the zero-length ester crosslinks from the crosslinked material. The material is preferably collagen.

As used herein, a zero-length crosslink is a direct bond between two functional groups on the material (e.g., collagen) without an intervening spacer molecule. These bonds are within the same material (e.g., polymeric material), but not necessarily within the same molecule or polymeric chain of the material.

In another embodiment of the invention, a method for crosslinking collagen-based material includes: providing a collagen-based material having collagen amine groups, collagen carboxyl groups, and collagen hydroxyl groups; blocking at least a portion of the collagen amine groups with a blocking agent to form blocked amine groups; activating at least a portion of the collagen carboxyl groups after forming blocked amine groups to form activated carboxyl groups; contacting the activated carboxyl groups with a polyfunctional spacer to crosslink the collagen-based material to form a crosslinked collagen-based material comprising spacer crosslinks and zero-length ester crosslinks; and removing at least a portion of the zero-length ester crosslinks from the crosslinked collagen-based material.

In yet another embodiment of the invention, a method for crosslinking material includes: providing a material having amine groups, carboxyl groups, and hydroxyl groups; blocking at least a portion of the amine groups with a blocking agent to form blocked amine groups; activating at least a portion of the carboxyl groups after forming blocked amine groups to form activated carboxyl groups; contacting the activated carboxyl groups with a polyfunctional spacer to crosslink the material to form a crosslinked material comprising spacer crosslinks and zero-length ester crosslinks; and removing at least a portion of the zero-length ester crosslinks from the crosslinked material.

In another embodiment of the invention, a method for making a bioprosthetic device (such as a heart valve) includes: providing a crosslinked collagen-based material having zero-length ester crosslinks and spacer crosslinks, wherein the collagen-based material included collagen amine groups, collagen carboxyl groups, and collagen hydroxyl groups prior to crosslinking; and removing at least a portion of the zero-length ester crosslinks from the crosslinked collagen-based material. Preferably, providing a crosslinked collagen-based material having zero-length ester crosslinks and spacer crosslinks comprises: providing a collagen-based material having collagen amine groups, collagen carboxyl groups, and collagen hydroxyl groups; blocking at least a portion of the collagen amine groups with a blocking agent to form blocked amine groups; activating at least a portion of the collagen carboxyl groups after forming blocked amine groups to form activated carboxyl groups; contacting the activated carboxyl groups with a polyfunctional spacer to crosslink the collagen-based material to form a crosslinked collagen-based material comprising spacer crosslinks and zero-length ester crosslinks.

In still another embodiment of the invention, a method for making a bioprosthetic device includes: providing a collagen-based material having collagen amine groups, collagen carboxyl groups, and collagen hydroxyl groups; blocking at least a portion of the collagen amine groups with a blocking agent to form blocked amine groups; activating at least a portion of the collagen carboxyl groups after forming blocked amine groups to form activated carboxyl groups; contacting the activated carboxyl groups with a polyfunctional spacer to crosslink the collagen-based material to form a crosslinked collagen-based material comprising spacer crosslinks and zero-length ester crosslinks; and removing at least a portion of the zero-length ester crosslinks from the crosslinked collagen-based material.

In the methods of the present invention, removing at least a portion of the zero-length ester crosslinks from the crosslinked material (preferably crosslinked collagen-based material) preferably includes exposing the crosslinked material to hydrolyzing conditions or an enzyme.

DETAILED DESCRIPTION OF ILLUSTRATIVE EMBODIMENTS

The present invention provides methods for making crosslinked materials, particularly crosslinked collagen-based materials, and bioprosthetic devices (typically an implant or implantable device), particularly bioprosthetic devices that include collagen-based materials.

In certain embodiments, methods involve removing zero-length ester crosslinks in crosslinked materials that prior to crosslinking included amine groups, carboxyl groups, and hydroxyl groups, such as collagen-based material. Alternatively, or additionally, methods involve blocking at least a portion of the amine groups to prevent the formation of zero-length crosslinks.

As used herein, a zero-length crosslink is a direct bond between two functional groups on the material (e.g., collagen) without an intervening spacer molecule. These bonds are within the same material (e.g., polymeric material), but not necessarily within the same molecule or polymeric chain of the material. Zero-length crosslinks can include ester groups that are formed from the reaction of carboxyl functional groups and hydroxyl functional groups. Alternatively, zero-length crosslinks can include amide groups that are formed from the reaction of carboxyl functional groups and amine functional groups.

For certain preferred embodiments, the present invention provides methods for making a bioprosthetic device made of collagen-based material, such as a heart valve, by crosslinking the collagen-based material with a polyfunctional spacer (preferably a bifunctional spacer). The resultant crosslinked material can also include zero-length crosslinking (i.e., direct bonding between reactive groups on the collagen without an intervening spacer molecule), which can reduce the flexibility of the material. Thus, the present invention is directed to removing and/or preventing such zero-length crosslinking in the crosslinked collagen-based material.

In one embodiment, the collagen-based material is initially crosslinked with a spacer molecule. More specifically, this involves first blocking at least a portion (and preferably, a majority) of the free collagen amine groups with one or more blocking agents, subsequently activating at least a portion (and preferably, a majority) of the collagen carboxyl groups with one or more activating reagents, and then contacting the activated collagen carboxyl groups with one or more polyfunctional spacers (preferably bifunctional spacers) to crosslink the collagen-based material. In this way, generally only the carboxyl groups, and few if any of the amine groups, of the collagen-based material are involved in crosslinking. Although such deactivation or blocking of the free collagen amine groups decreases the formation of zero-length amide crosslinks by reaction of activated carboxyl groups with free amine groups of collagen, there can still be zero-length crosslinks present as a result of activated carboxyl groups with free hydroxyl groups of collagen. It is desirable to prevent or reduce the number of such crosslinks.

Removing zero-length crosslinks and/or preventing the formation of zero-length crosslinks is advantageous because a large number of zero-length crosslinks makes collagenous materials stiff and brittle, which is in contrast to the desired mechanical properties of a bioprosthetic device.

For certain embodiments, preferably, the methods that involve removing zero-length crosslinks involve removing at least 30%, and more preferably, at least 50%, of the zero-length ester crosslinks. Even more preferably, the methods remove at least 70% of the zero-length ester crosslinks, even more preferably, at least 80% of the zero-length ester crosslinks, and most preferably, at least 90% of the zero-length ester crosslinks.

The removal of, or prevention of the formation of, zero-length crosslinks, generally provides materials with desirable biomechanical properties. For example, reducing the number of zero-length crosslinks can improve the flexibility of the crosslinked material. The materials of the present invention are preferably collagen-based materials, which are preferably used to form bioprosthetic devices. Although the present invention is described herein with reference to collagen-based materials and bioprosthetic devices, the methods can be used in a variety of other materials that include at least amine functional groups, carboxyl groups, and hydroxyl groups. Examples of such materials that can be prepared using the methods of the present invention include functional proteins, antibodies, aminoglycans.

Herein, a bioprosthetic device is typically derived in whole or in part from natural tissues that contain collagen-based materials (often simply referred to herein as "collagen"). Such bioprosthetic devices include, for example, heart valves and other heart components, vascular replacements or grafts, urinary tract and bladder replacements, bowel and tissue resections, tendon replacements, and the like. Such collagen-based materials include whole tissue (i.e., tissue containing collagen and non-collagenous substances or cells), only the collagen matrix without the non-collagenous substances, and purified fibrous collagen. Typically, and preferably, however, whole tissues are used in making bioprosthetic implants.

In one embodiment of the invention, a method for making a material includes: providing a crosslinked material (preferably a crosslinked collagen-based material) having zero-length ester crosslinks and spacer crosslinks, wherein the material included amine groups, carboxyl groups, and hydroxyl groups prior to crosslinking; and removing at least a portion of the zero-length ester crosslinks from the crosslinked material.

Preferably, removing at least a portion of the zero-length ester crosslinks from the crosslinked material preferably includes exposing the crosslinked material to hydrolyzing conditions or an enzyme. Preferably, hydrolyzing conditions are used to remove at least a portion of the zero-length ester crosslinks.

In certain embodiments, methods of the present invention involve removing at least a portion of the zero-length ester crosslinks by exposing the crosslinked material to an initial temperature of preferably at least 2° C., more preferably at least 4° C., even more preferably at least 10° C., and even more preferably at least 18° C. In certain embodiments, methods of the present invention involve removing at least a portion of the zero-length ester crosslinks by exposing the crosslinked material to an initial temperature of preferably at most 60° C., more preferably at most 50° C., even more preferably at most 45° C., and even more preferably at most 40° C. Typically, the reaction is carried out at 37° C.

In certain embodiments, methods of the present invention involve removing at least a portion of the zero-length ester crosslinks by exposing the crosslinked material to an initial pH of preferably at least 2, and more preferably at least 7. In certain embodiments, methods of the present invention involve removing at least a portion of the zero-length ester crosslinks by exposing the crosslinked material to an initial pH of preferably at most 11, and more preferably at most 9.

In certain embodiments, methods of the present invention involve removing at least a portion of the zero-length ester crosslinks by exposing the crosslinked material to a buffered solution. Buffering helps stabilize the material and prevents damage to the material. In certain embodiments, the buffered solution is acidic. In certain other embodiments, the buffered solution is basic.

Examples of reagents used for acidic hydrolysis include, but are not limited to, hydrochloric acid, ferroacidic acid, acetic acid, phosphoric acid, and combinations thereof.

Examples of reagents used for basic hydrolysis include, but are not limited to, alkali metal (e.g., sodium and potassium) phosphates, sodium borate, sodium carbonate, sodium hydrogen carbonate, and combinations thereof.

Preferably, the osmolality of the hydrolyzing composition (e.g., acidic or basic buffered solution) is controlled to prevent the material from drying out, swelling, shrinking, etc. This can be done with a salt, for example.

Enzymes can also be used to remove zero-length ester crosslinks. Although suitable enzymes can include hydrolazes for hydrolyzing the ester bonds, other enzymes can also be used that do not necessarily involve hydrolysis. Examples include, but are not limited to, esterases, lipases, and the like.

Crosslinked material can be prepared by a number of methods. Typically, it can be prepared by providing a material with amine groups, carboxyl groups, and hydroxyl groups, optionally blocking at least a portion of the amine groups, activating at least a portion of the carboxyl groups, and crosslinking the activated carboxyl groups with a polyfunctional spacer.

Specifically, in one embodiment of the invention, a method for crosslinking collagen-based material includes: providing a collagen-based material having collagen amine groups, collagen carboxyl groups, and collagen hydroxyl groups; blocking at least a portion of the collagen amine groups with a blocking agent to form blocked amine groups; activating at least a portion of the collagen carboxyl groups after forming blocked amine groups to form activated carboxyl groups; and contacting the activated carboxyl groups with a polyfunctional spacer to crosslink the collagen-based material to form a crosslinked collagen-based material with spacer crosslinks.

In certain methods of the present invention the free amine groups of the collagen-based materials (often simply referred to herein as "collagen"), or other materials, can be blocked by various types of chemical reagents prior to crosslinking. The four major types of reactions through which blocking of free amines can be achieved are: (1) acylation reaction; (2) amination reaction, preferably involving reductive amination using aldehydes or ketones; (3) amination reaction using epoxides; and (4) amination reaction with sulphonyl or sulphonic acid derivatives. Preferably, small blocking agents, i.e., those having two to six carbon atoms in length, are used in order to prevent significant disruption of the native triple helix structure of the collagen. Although such reactions involving the use of small blocking agents are preferred, biologically active compounds can also be used to block the free amine groups.

There are numerous acylating agents for use in blocking the amine groups using the acylation reaction. Of particular importance are the isocyanates, isothiocyanates, acid halides, acid anhydrides, activated esters (i.e., esters with a good leaving group easily released upon reaction with an amine) such as N-hydroxysuccinimide ester, and imidoesters. The ester and imidoester reagents are the most preferred. Many esters are readily available, relatively easy to prepare, and more stable, when compared to the corresponding acyl halide or anhydride.

Imidoesters are very specific towards amino groups. In mild alkaline conditions they react with amines to form imidoamines; the products carry a positive charge at physiological pH. Amidation therefore retains the net charges of the protein minimizing the effect of charge on protein conformation. Isocyanates and isothiocyanates react with amino groups, but also with sulfhydryl, imidazolyl, tyrosyl, and carboxyl groups of proteins. Although only amino groups yield stable products, these acylating agents are less specific than activated esters or imidoesters.

Preferred acylating agents include, but are not limited to: N-hydroxy succinimide esters (NHS), such as acetic acid N-hydroxysuccinimide ester, sulfo-NHS-acetate, and propionic acid N-hydroxysuccinimide ester; p-nitrophenyl esters such as p-nitrophenyl formate, p-nitrophenyl acetate, and p-nitrophenyl butyrate; 1-acetylimidazole; and citraconic anhydride (reversible blocker).

There are numerous aminating agents (e.g., alkylating agents) for use in blocking the amine groups using the amination reaction. Particularly preferred are aldehydes and ketones. Reaction of a free amine with an aldehyde or ketone yields an imine (or Schiff base) that is quite stable (particularly when an aryl group is present). If necessary, however, the formed imine can be further stabilized through reduction with reducing agents like sodium cyanoborohydride, sodium borohydride, or borane reagents such as dimethylamine borane, trimethylamine borane or morpholine borane.

Aldehydes are preferred aminating agents because ketones generally react more slowly and often require higher temperatures and longer reaction times. A wide variety of aldehydes can be used. Preferably, the aldehydes are monofunctional aldehydes to avoid undesirable crosslinking. Examples of monofunctional aldehydes include, but are not limited to, propanal, butanal, and hexanal (caproaldehyde).

When using an aminating agent, the structure formed is a secondary amine, which, theoretically, could react with activated carboxyls. It has been surprisingly discovered, however, that these secondary amine groups are sufficiently sterically hindered that, under typical reaction conditions, crosslinking does not occur.

Epoxides can be also used as the aminating agent to block the amine groups. An epoxide also forms a secondary amine; however, it is anticipated that such groups will also be sufficiently sterically hindered that, under typical reaction conditions, crosslinking will not occur. Preferably, the epoxide is a monofunctional epoxide. Suitable epoxides include, for example, iso-propylglycidylether and n-butylglycidylether. The use of an epoxide as the blocking agent is less desirable because the reaction tends to be slow and less effective.

Sulphonyl or sulphonic acid derivatives are another group of aminating agents that may be used to block free amine groups. Preferably, the sulphonyl or sulphonic acid derivative is monofunctional. An exemplary reagent is 2,4,6-trinitrobenzenesulfonic acid, for example.

A wide variety of biologically active derivatives of such compounds (i.e., those containing an appropriate reactive moiety such as an ester, aldehyde, or ketone, for example) can be used to block the free amine groups. As a result, desirable biological functions can be included into the collagenous matrix that may improve biocompatibility and overall performance. An example is aldehyde-functional heparin, obtained either through periodate oxidation (periodate-heparin) or nitrous acid degradation (NAD-heparin).

Preferably, the methods of the present invention include blocking the free amine groups using an acylation reaction or an amination reaction. Considering ease of operation and blocking efficacy, more preferably, blocking the free collagen amine groups is done through the use of activated esters like acetic acid N-hydroxysuccinimide (HAc—NHS) (for acylation) or short-chained aliphatic monofunctional aldehydes like propanal or butanal (for amination (e.g., alkylation)).

In some embodiments, the acylating agents may be preferred because they are capable of blocking a majority of the free amine groups with substantially no distortion of the collagen triple helix configuration. This is an important selection criteria for the choice of blocking agent and can be determined readily easily. Calorimetry, for instance, can be used to determine the extent to which blocking has disrupted the native triple helix configuration of the collagen. Disruption of the triple helix is denoted by a decrease of the onset of the collagen denaturation temperature.

A mixture of the above amine blocking agents can be used in the methods of the present invention. The amine blocking agent (or mixture of blocking agents) is used in an amount effective to block at least a portion, preferably, a majority (i.e., greater than 50%), of the free amine groups. More preferably, the blocking agent(s) is used in a significant molar excess relative to the number of free amine groups.

The amine blocking reaction is preferably carried out in an aqueous solution, and more preferably, in a buffered aqueous solution having a pH of at least 6, and more preferably no greater than 7. The temperature of this reaction should be below that at which the collagen-based material is denatured. Thus, although increased temperatures do increase reaction rates, the reaction is preferably performed at room temperature (i.e., 20–25° C.), and more preferably, at 21° C.

Preferably, such amine blocking agents are capable of blocking at least 75% of the free collagen amine groups, more preferably, at least 80%, and most preferably, at least 90%, of the free collagen amine groups. Such deactivation or blocking of the free collagen amine groups decreases the formation of zero-length crosslinks, i.e., reaction of activated carboxyl groups with free amine groups of collagen. This is advantageous because a large number of zero-length crosslinks makes collagenous materials stiff and brittle, which is in contrast to the desired mechanical properties of a bioprosthetic device.

Typically, the relatively small number of free amine groups that are not blocked are not easily accessible due to steric hindrance, and as such would not be able to participate in zero-length crosslinking. Another favorable aspect is the fact that it is believed that blocking the amine groups provides improvement in the biocompatibility of the collagen-based material because free amine groups have been suggested to be involved in the immune response.

Once the free amine groups are sufficiently blocked, the free carboxyl groups can be crosslinked. This is done by first activating the carboxyl groups. Preferably, this is done by initially contacting the material (preferably collagen-based material) with the crosslinking agent (i.e., spacer), and allowing it to penetrate into the material, and then activating the carboxyl groups, which allows for interaction with the crosslinking agent.

The free carboxyl groups can be activated by a variety of methods. Carbodiimide reagents are well-known activating agents and traditionally most often used. Reaction between a carboxyl group and a carbodiimide yields the reactive intermediate O-acylisourea; this intermediate is prone to a nucleophilic attack in a subsequent step. In addition, an intramolecular rearrangement reaction in which the O-acylisourea rearranges to the much more stable, and much less reactive, N-acylurea may happen. Under typical reaction conditions, the half-life of the O-acylisourea is in the range of seconds to minutes.

This reactive O-acylisourea can be stabilized through the use of a succinimide or other stabilizing agents. Using a stabilizing agent in addition to the activating agent can increase the half-life of the O-acylisourea to 30–40 minutes under typical reaction conditions. Also, significantly, the intramolecular rearrangement reaction is suppressed. Typically, these stabilizing agents themselves are also capable of activating the carboxyl groups, although much less effectively than when combined with carbodiimides.

Examples of activating agents other than carbodiimide include, but are not limited to, those typically used in peptide synthesis. Examples include 1,1'-carbonyldiimidazole (CDI), N,N'-disuccinimidyl carbonate (DSC), 2-ethoxy-1-ethoxycarbonyl-1,2-dihydroqu inoline (EEDQ), and 1,2-benzisoxazol-3-yl-diphenyl phosphate (BDP), and N-ethyl-5-phenylisoxazolium-s'-sulfonate (Woodwards Reagent K). Such activating agents are at least partially soluble in water. Although activating agents that are not at least partially water soluble, such as azides (e.g., diphenylphophorylazide as disclosed in U.S. Pat. No. 5,264,551 (Petite et al.)), can be used in the method of the present invention, they are not particularly desirable. Mixtures of activating agents can be used.

Preferably, the free carboxyl groups are activated by contacting them with a carbodiimide that is at least partially soluble in water. A particularly preferred water-soluble carbodiimide suitable for use in the present invention is 1-ethyl-3-(3-dimethylaminopropyl) carbodiimide.HCl (EDC). Other suitable carbodiimides include, for example, cyanamide and N,N'-dicyclohexylcarbodiimide (DCC), N,N'-diisopropylcarbodiimide (DIC), and 1-cyclohexyl-3-(2-morpholinoethyl) carbodiimide metho-p-toluenesulfonate (CMC).

As stated above, when a carbodiimide is used to activate the carboxyl groups, O-acylisourea groups are formed that can rearrange to less reactive N-acylurea groups. The addition of N-hydroxysuccinimide (NHS) is known to decrease this tendency for rearrangement. Other stabilizing agents, such as N-hydroxybenzotriazole (HOBt), N-hydroxy-5-norbornene-endo-2,3-dicarboximide (HONB), 4-dimethylaminopyridine (DMAP), and the sulfo-derivative of N-hydroxysuccinimide, are also capable of accomplishing this. Mixtures of such stabilizing agents can be used. In particularly preferred methods of the present invention, the collagen carboxyl groups are activated using a mixture of a carbodiimide (preferably, EDC) and NHS.

Various mixtures of the above activating agents and optional stabilizing agents can be used in the methods of the present invention. The activating agent or agents are used in amounts effective to activate at least a portion, and preferably, a majority (i.e., greater than 50%), of the free carboxyl groups. More preferably, the activating agent or agents are used in a molar excess relative to the number of free carboxyl groups. The stabilizing agent or agents are used in an amount effective to stabilize a majority of the activated carboxyl groups. Preferably, the stabilizing agent or agents are used in an amount of at least a level that equals the number of free carboxyl groups. More preferably, the stabilizing agent or agents are used in a molar excess relative to the number of free carboxyl groups, but preferably not exceeding the molar level of the activating agent or agents.

The activating reaction is preferably carried out in an aqueous solution, more preferably, a buffered aqueous solution having a pH of preferably at least 4, and more preferably at least 5. The activating reaction is preferably carried out in an aqueous solution, more preferably, a buffered aqueous solution having a pH of preferably no greater than 9, more preferably no greater than 7, and even more preferably no greater than 6. The temperature of this reaction should be below that at which the collagen-based material is denatured. Thus, although increased temperatures do increase reaction rates, the reaction is preferably performed at room temperature, and more preferably, at 21° C.

The activated carboxyl groups are then reacted with a polyfunctional spacer (preferably a bifunctional spacer) to crosslink the collagen-based material. It is believed that the introduction of spacers allows the formation of crosslinks that not only bridge the distance between two adjacent collagen fibers or fiber bundles, but also introduce extra flexibility into the whole matrix. Preferably, the bifunctional spacer is a diamine spacer, although other bifunctional spacers can be used such as diepoxides and diesters. More preferably, the bifunctional spacer is a diamine spacer of largely hydrophilic nature, soluble in aqueous solutions, with the reactive moieties preferably located at the respective ends of the longest molecular chain. The spacers may be straight-chained or branched-chained, appropriately substituted compounds. Further substitutions in the chain should not interfere with the crosslinking process and/or diminish the solubility of the spacers in aqueous solutions. Hydrophilicity of the spacer is believed to be advantageous as this can effect infiltration and diffusion of tissue fluid through the bioprosthetic matrix.

Suitable hydrophilic diamine spacers include, for example, the diamine derivatives of polyethyleneglycol and polypropyleneglycol oligomers and polymers, and polyethylene-polypropyleneglycol copolymers, such as for example O,O'-bis(3-aminopropyl)diethyleneglycol, O,O'-bis(2-aminopropyl)polypropyleneglycol, and O,O'-bis(2-aminopropyl)polyethyleneglycol. Furthermore, aliphatic diamines of two to eight carbon atoms in length are suitable spacers. This includes compounds with substitutions in the carbon chain, such as, for example, 1,4-diaminobutane, 1,6-diaminohexane, and 1,5-diamino-2-methylpentane. A preferred class of hydrophilic diamine spacers include polyethyleneglycol spacers, polypropyleneglycol spacers, and polyethylenepropyleneglycol spacers, which can be represented by the following general formula:

$H_2N—CH(CH_3)—CH—[OCH_2CH(CH_3)]_x—$
$[OCH_2CH_2]_y—[OCH_2CH(CH_3)]_z—NH_2$ wherein: x+z=0–70 and y=0–90; preferably, x+z=0–35 and y=0–45. Such spacers are commercially available from a variety of sources, such as Aldrich Chemical Co., and Huntsman, under the trade designation "JEFFAMINE." Such compounds are highly hydrophilic polymers having a widely varying, but well characterized, molecular weight.

The use of hydrophilic spacers can advantageously render the crosslinked material hydrophilic. As stated above, this is believed to effect proper infiltration and diffusion of tissue fluid through the bioprosthetic matrix. This provides a supply of oxygen, nutritive substances, and electrolytes into the tissue, as well as drainage of metabolized substances from the tissue. As a result, the growth of capillary blood vessels and cells will be promoted, and consequently a good healing response to the implanted material.

Additionally, it is believed that crosslinking agents having a highly flexible, long-chain structure will effect crosslinking in between adjacent fibers and fiber bundles, which will have a beneficial effect on the mechanical properties of the resultant crosslinked material.

The spacer(s) are used in amounts effective to crosslink a desired number of the activated carboxyl groups. Preferably, this amount involves a molar ratio of the bifunctional spacer(s) relative to the number of activated carboxylic groups of at least 1:2, and more preferably of 1:1.

The crosslinking reaction is preferably carried out in an aqueous solution, and more preferably, a buffered aqueous solution having a pH of preferably at least 4, and more preferably at least 5. The crosslinking reaction is preferably carried out in an aqueous solution, and more preferably, a buffered aqueous solution having a pH of preferably no greater than 9, more preferably no greater than 7, and even more preferably no greater than 6. The temperature of this reaction should be below that at which the collagen-based material is denatured. Thus, although increased temperatures do increase reaction rates, the reaction is preferably performed at room temperature, and more preferably, at 21° C.

Preferably, the methods of the present invention involve initially blocking of the free collagen amine groups, contacting the collagen-based material with the spacer molecules to allow them to imbibe (i.e., penetrate) the collagen-based material, and then activating the collagen carboxyl groups toward the spacer molecules. Imbibement of the collagenous material prior to addition of the reagents that activate the carboxyl groups toward the spacer molecules significantly enhances the efficacy of the crosslinking process. This step typically is carried out in 15 minutes. The temperature of this imbibing step should be below that at which the collagen-based material is denatured. Thus, although increased temperatures do increase the rate of imbibement, the reaction is preferably performed at room temperature, and more preferably, at 21° C.

Crosslinking of collagen-based materials according to the methods of the present invention yield a material with a generally high degree of crosslinking and a generally high resistance toward enzymatic digestion, while the material maintains a relatively high degree of flexibility without substantial stiffening over time. This material is also preferably highly hydrophilic, which is believed to increase the biocompatibility of the material. The great reduction in free amine groups also contributes to a better biocompatibility by lowering the antigenic potential of the material. As discussed before, the biocompatibility of this material can also be improved by blocking the amine groups with appropriate biologically active molecules, such as for instance, the very blood compatible molecule heparin, instead of using small biologically non-active molecules. These properties make the method according to the present invention particularly suitable for crosslinking of cardiovascular bioprostheses, such as heart valves and vascular grafts.

The invention will be further described by reference to the following detailed examples. These examples are offered to further illustrate the various specific and illustrative embodiments and techniques. It should be understood, however, that many variations and modifications may be made while remaining within the scope of the present invention.

EXPERIMENTAL EXAMPLES

Materials and Methods

Preparation of Tissue

To prepare "Native" tissue samples, fresh porcine aortic root tissue, obtained from a slaughterhouse (Premium Fleish, Emsland, Germany or Bleijlevens, Kerkrade, the Netherlands) was rinsed free of blood with an exces buffered 0.01 M N-(2-hydroxyethyl)piperazine-N'-2-ethane sulfonic acid (HEPES) physiological saline solution (Sigma Aldrich, Zwijndrecht, Netherlands) and trimmed to remove excess myocardium and adventitial tissue. The resulting valves were then rinsed for at least 24 hours (maximum 48 hours) in 10 millimolar (mM) HEPES buffered saline (pH 7.4, 4° C.).

Blocking of Free Amine Groups by Reductive Amination

Free amine groups were blocked by reductive amination with a monofunctional aldehyde under reductive conditions according to the following reaction:

Propional, a monofunctional aldehyde reagent, was allowed to react with the amine groups of the collagen backbone under reactive conditions. For reaction conditions, see below.

Activating Carbonyl Groups and Crosslinking

To form crosslinks, tissue was reacted with a diamine spacer. Without being held to any particular theory, it is believed that by allowing the spacer molecule to penetrate into the tissue before the cross-linking reaction is initiated, part of the diffusion limitation that occurs primarily in the tissue wall is overcome.

The spacer molecule that was selected for this reaction is an amine terminated polypropylene glycol, commercially available under the trade name JEFFAMINE polyoxyalkyleneamines. JEFFAMINE polyoxyalkyleneamines contain primary amino groups attached to the terminus of a polyether backbone. The polyether backbone is based either on propylene oxide (PO), ethylene oxide (EO), or mixed EO/PO. The JEFFAMINES used in the present examples were amine-terminated polypropylene glycols (so called D-JEFFAMINES) having the following formula:

The spacer was selected because of its high intrinsic hydrophilicity and flexibility. A hydrophilic spacer is typically preferred because it has to penetrate deep in the tissue and, without being held to any particular theory, it is believed that the more hydrophilic the tissue becomes, the better tissue fluid infiltrates and diffuses through the tissue, whereby also the in-growth of capillary blood vessels is promoted. Moreover, it is believed that cross-linking with spacers such as polyoxyalkyleneamines will typically lead to longer chains between crosslinks, which is believed to provide a benefit by reducing the stiffness of the tissue.

To activate the carboxyl groups of aspartic acid and glutamic acid residues of the collagen tissue samples, water soluble carbodiimide (EDC) with the addition of N-hydroxysuccinimide (NHS) was used. NHS is believed to increase the efficacy of the activation reaction by suppressing the formation of the by-product N-acylurea that is typically formed after intramolecular rearrangement of compound (a), below, and forming a stable activated carboxyl ester (compound (b), below) that typically has a half life of about 30 minutes, instead of a half life of a few seconds typically observed under the reaction conditions that are employed (pH 5.0).

Under the foregoing conditions, it is believed that the ε-amine groups of lysine and hydroxylysine will generally be blocked, and primarily the free amines of the JEFFAMINE polyoxyalkyleneamines will react, preventing formation of zero-length crosslinks between the amine and the carboxyl groups of the collagen matrix. Such zero-length crosslinks are believed to be related to stiffening of the matrix.

Example 1

Crosslinking without Blocking ("EDC only")

A sample of the prepared Native valve tissue was immersed in 100 ml of a 0.25 Molar (M) 2-(N-morpholino) ethanesulfonic acid (MES) buffered solution (pH 5.0) containing 0.06 M JEFFAMINE 230 polyoxyalkyleneamine (Aldrich, Zwijndrecht, The Netherlands), 0.30 M 1-ethyl-3-(3-diethylaminopropyl)carbodiimide.HCl (EDC, Aldrich, the Netherlands) and 0.06 M N-hydroxysuccinimide (NHS, Aldrich, the Netherlands) and allowed to react for 48 hours at ambient conditions. The tissue was then rinsed in physiologic saline three times over a period of 24 hours, 8 hours in between, and stored individually at room temperature in 100 ml of 10 mM HEPES (pH 7.4) containing 20 weight percent (wt %) isopropyl alcohol (IPA).

The tissue sample was removed from storage, a disk of approximately 8 millimeter (mm) diameter was punched out of the sample, and an approximately 10 micrometer (μm) thick slice was made using a cryotome. Three (3) slices of the same sample were placed on a microscope slide and exposed to a fluorescent dye (A1400, Molecular Probes, Leiden, the Netherlands for approximately five (5) minutes by applying a drop of diluted dye solution on the sample (according to the instructions). The microscope slide was then exposed to a broad range frequency UV light source (Philips, Eindhoven Netherlands). A digital picture was taken (with a camera with fixed aperture and focus setting) and the intensity of the sample was calculated using software (Paint Shop Pro 7, Jasc software, Minneapolis USA).

Example 2

Blocking and Crosslinking ("IdeFix")

A sample of the prepared Native valve tissue was transferred to 100 milliliters (ml) of a solution of a 0.25 M MES buffer (pH 6.5) containing 0.5 M propional (Aldrich, The Netherlands) and 16 mM sodium cyanoborohydride (NaCNBH$_3$) (Aldrich, The Netherlands). The tissue was allowed to react in the solution for a total of 48 hours under ambient conditions with the addition of NaCNBH$_3$ to a total concentration of 32 mM at hour 6 and the addition of NaCNBH$_3$ giving a total concentration of 48 mM at hour 24. The tissue sample was then rinsed five times in exces physiological saline over a period of 24 hours.

The sample was then crosslinked according to Example 1, and a sample slice was prepared, exposed to a fluorescent dye, exposed to a light source, and the sample intensity calculated according to Example 1.

Example 3

Blocking, Crosslinking, and Exposure to a Basic Buffer ("IdeFix+Base")

A sample was prepared, blocked, crosslinked, and exposed to a fluorescent dye according to Example 2, except that after the sample was crosslinked, the tissue sample was transferred to 100 ml of a 0.1 M Na$_2$BO$_4$ buffer solution, pH 9.2 (Aldrich, The Netherlands) and allowed to react for 24 hours at ambient conditions. The tissue sample was then removed from the borate buffer solution, rinsed in 100 ml of 10 mM HEPES, pH 7.4 (ambient conditions for 30 minutes), then transferred to a sterilization solution (20% IPA in 10 mM HEPES solution). The sample was then prepared, exposed to a fluorescent dye, exposed to a light source, and the sample intensity calculated according to Example 2.

Example 4

Blocking, Crosslinking, and Exposure to an Acid Buffer ("IdeFix+Acid")

A sample was prepared according to Example 3, except that instead of transferring the tissues to a borate buffer solution, the samples were transferred to 100 ml of a 0.1 M acetic acid buffer (pH 3, 0.1 M Acetic acid, Aldrich, the Netherlands).

Example 5

Crosslinking, and Exposure to a Basic Buffer ("EDC Only+Base")

A sample was prepared according to Example 4, except that the blocking step was not performed and instead of an acetic acid buffer a borate buffer (0.1 M, pH 9.2, Aldrich, the Netherlands) was used.

Example 6

Crosslinking, and Exposure to an Acidic Buffer ("EDC Only+Acid")

A sample was prepared according to Example 4, except that the blocking step was not performed.

Example 7

Native Tissue ("Native")

Slices of the native prepared valve tissue, was prepared, exposed to a fluorescent dye, exposed to a light source, and the sample intensity calculated according to Example 1.

Determination of Carboxyl Groups Using a Fluorescent Dye.

Figure 1:
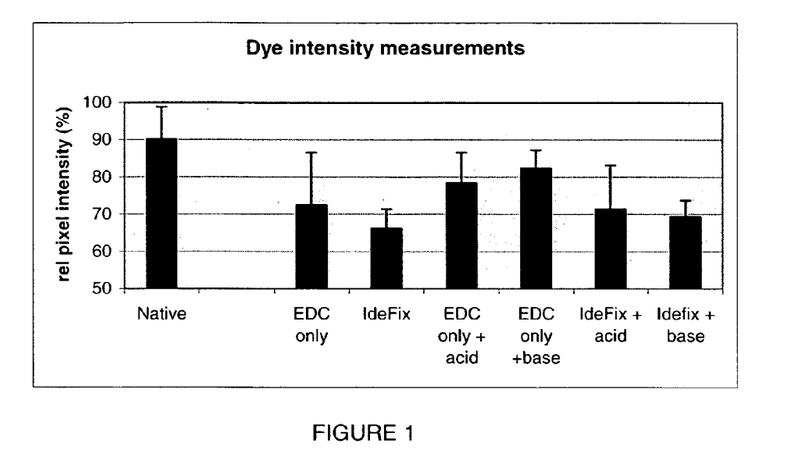
FIG. 1. Signal intensity measurements after exposing the samples to a fluorescent dye.

The results of each of Examples 1–7 are depicted in FIG. 1. The Y-axis shows the "pixel intensity." The higher the value, the greater number of free carboxyl groups are present on the tissue sample. Results show that, compared with the Native sample, the number of free carboxyl groups decreased after cross-linking with EDC (all samples except the Native sample). Free carboxyl groups were then retrieved after exposure of the samples to an acid or base buffer. However, the "IdeFix" crosslinked samples indicated that fewer carboxyl groups were available, both before and after exposure to an acid or base buffer, as compared with the "EDC only" samples.

Without being held to any particular theory, it is believed that during activated crosslinking of the "EDC only" samples, the carboxyl groups formed crosslinks with amine groups or with hydroxyl groups. It was assumed that if the source of amine groups is collagen related, a relatively large amount of hydroxyl groups are crosslinked.

In the "IdeFix" sample, however since collagen related amine groups were blocked, the amine group source was due to a relatively high concentration of JEFFAMINE polyoxyalkyleneamine present in the matrix. Since these groups are more accessible for the carboxyl groups it was believed that this amine group source would react to a greater extent. This resulted in a greater number of carboxyl groups becoming available in the "EDC only" sample subsequently treated with an acidic or basic buffer as compared with the "IdeFix" treated sample subsequently treated with an acidic or basic buffer.

Example 8 pH Range of De-esterification Post-treatment

The following examples provide supportive data for the "IdeFix" post-treatment to remove undesirable ester bonds formed during the crosslinking process. By using native collagen without any chemical crosslinking process applied, the most 'delicate' sample configuration was chosen. If collagen is susceptible for changes as a result of de-esterification post-treatment, it would likely appear strongest in a native form of collagen.

Subsequent to incubation at a specified pH in the examples below, shrink temperature was measured using differential scanning calorimetry to evaluate changes in the physical or chemical properties of the collagen. The shrink temperature is defined at the onset of the shrink peak, i.e., where the tangent in the inflection point of the upward slope crossed the extended in baseline. Native collagen content is measured by exposing the collagen to a trypsin solution that fragmentates and dissolves denatured collagen.

Bovine collagen tissue (Coletica, France) was obtained and a sample of 1 centimeter (cm)×6 cm (tissue was incubated at 37° C. in physiological buffered saline solution (acetic acid) at pH 3 for 24 hours, under mild continuous shaking The sample was then rinsed in deionized water and frozen at −20° C., then freeze-dried (24 hours HETO, Germany).

The amount of native collagen (NCC) was determined using trypsin degradation and determination of the total amino acid content using HPLC.

Examples 9–15

Figure 2:
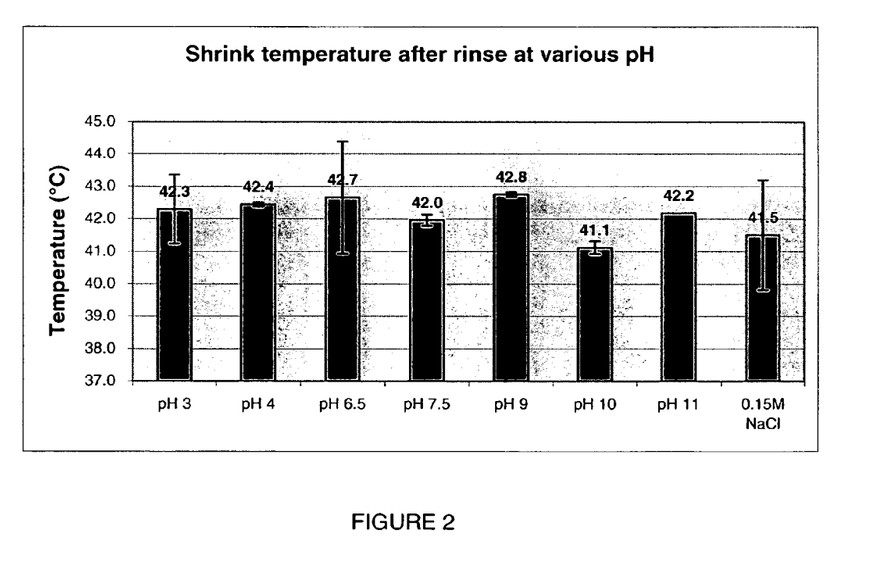
FIG. 2. Chart of shrink temperatures relative to pH after post-treatment to remove undesirable ester bonds formed during the crosslinking process.

Example 8 was repeated seven times in the same manner as described above, at each of pH 4, 6.5, 7.5, 9, 10, 11, and in f 0.15 M NaCl in place of the pH 3 buffered solution. The results are given in Table 1, below, and in FIG. 2.

TABLE 1

| treatment | T shrink (° C.) | stdev | native collagen (%)* |
|---|---|---|---|
| pH 3 | 42.3 | 1.1 | 89.9 |
| pH 4 | 42.4 | 0.1 | 90.8 |
| PH 6.5 | 42.7 | 1.7 | 92.0 |
| PH 7.5 | 42.0 | 0.2 | 93.5 |
| pH 9 | 42.8 | 0.1 | 91.7 |
| pH 10 | 41.1 | 0.2 | 90.0 |
| pH 11 | 42.2 | | 91.4 |
| 0.15M NaCl | 41.5 | 1.7 | 94.7 |

*Typically, native collagen content measurements have a 2.5% error

From both shrink temperatures (FIG. 2) and native collagen contents (Table 1), it can be concluded that the pH range of 3 to 11 is a range that is well tolerated by native collagen, since no significant changes were observed in shrink temperature or native collagen content. Therefore it should also provide a safe working range for crosslinked tissue, such as heart valves, in that the basic structure and properties of the collagen were not adversely affected by the post-treatment.

Examples 16–18

Uni-axial Mechanical Behavior of Crosslinked Bovine Pericardium

To evaluate the effect of de-esterification post-treatment on mechanical properties of crosslinked tissue, fresh bovine pericardium was treated and subsequently analyzed by means of a uni-axial pull test method. Hereto samples were cut (1 cm×5 cm) and tested using a uni-axial pull test system with a 50N load cell (Zwick, Ulm, Germany)

Example 16

IdeFix Treatment of Pericardium

Bovine pericardium tissue was obtained (Bleijlevens Kerkrade, the Netherlands) and prepared by rinsing overnight in ice-cold saline solution (at 0° C.).

After dissection, the pericardium sample was treated with 0.5 M propionaldehyde/50 millimolar (mM) sodium cyanoborohydride (see above) in MES buffer pH 6.4 for 2 hours, then rinsed in physiological saline solution for two hours. The sample was then crosslinked using 60 mM JEFFAMINE 230, 300 mM EDC and 120 mM NHS in MES buffer (all Aldrich, Zwijndrecht, the Netherlands pH 5.0 for 2 hours.

A test sample of 1 centimeter (cm) wide by approximately 5 cm long having an average thickness of 0.3 mm was then taken from the crosslinked bovine pericardium and evaluated using a vertical pull test. Pneumatic grips with a lining of emery paper were used to clamp the sample at a fixed with of 3 cm, allowing 1 cm on each side to clamp between the grips. Care was taken to maintain the sample in hydrated condition. The sample was pulled with a constant speed of 5 millimeter/minute, until a force of 50 N was recorded. Stress-strain curves were recorded, and low strain tissue modulus in Newtons per square millimeter (N/mm$^2$) were calculated between 1 and 5 N force. The test was performed on three different samples.

Example 17

IdeFix with Post-treatment

Example 16 was followed, except that after crosslinking with JEFFAMINE, EDC, and NHS in the MES buffer, the sample was allowed to stay overnight in a solution of 4 wt % NaHCO$_3$ (Aldrich, the Netherlands) Three test samples of the tissue were then prepared and subjected to the vertical pull test as described in Example 16.

Example 18

Treatment with Glutaraldehyde

Bovine pericardium tissue was obtained and prepared as in Example 16. The tissue was then treated with a solution of 0.2 M glutaraldehyde in MES buffer (pH 6.4) for at least 72 hours. Four test samples of the tissue were then prepared and subjected to the vertical pull test as described in Example 16.

Figure 3:
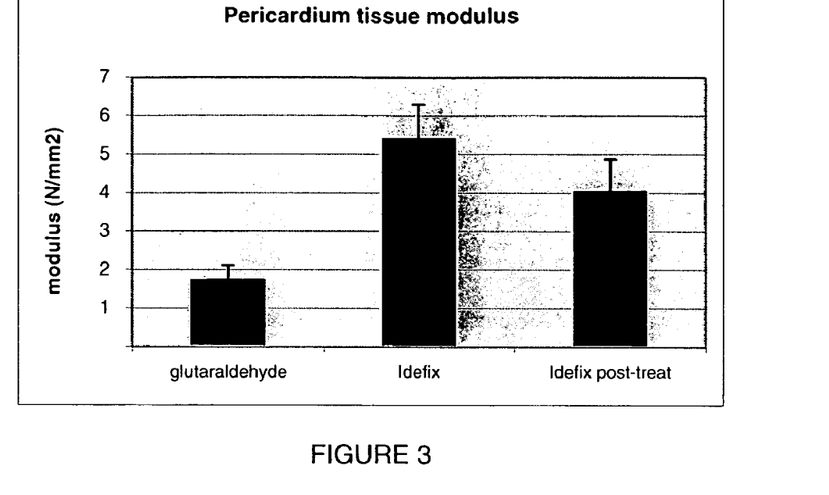
FIG. 3. Chart of pericardium tissue modulus after various treatments.

The resulting values of Examples 16–18 are given in Table 2, below, and in FIG. 3.

TABLE 2

| | low-strain modulus (N/mm$^2$) | stdev |
|---|---|---|
| glutaraldehyde | 1.79 | 0.33 |
| Idefix | 5.46 | 0.83 |
| Idefix post-treat | 4.10 | 0.78 |

The post-treatment results in a decreased modulus compared to standard Idefix, indicating a change in elastic behavior. The post-treatment has resulting in a 25% decrease in modulus compared to Idefix, which is one-third of the measured difference between glutaraldehyde and Idefix treatment.

Examples 19–22

Ester Formation Via Carbodiimide Chemistry

The following examples indicated that the use of carbodiimide did induce ester bond formation between alcohol and carboxyl moieties in an aqueous environment. Furthermore it is indicated that a mild hydrolysis treatment allows breaking of the ester bonds. This treatment is performed at a pH and temperature where breaking of amide bonds is not expected to occur.

Example 19

Coupling of D-AN to SEPHADEX CM Gel

As a model for the carboxyl group containing part of collagen, SEPHADEX CM gel was chosen. SEPHADEX CM gel is a dextran derivative, crosslinked with epichlorhydrin via ether bonds and modified with carboxymethyl groups, giving carboxyl groups attached to the matrix via ether bonds. Thus a hydrolytically stable hydrogel is formed with an abundance of pendant carboxyl groups.

As a model for pendant hydroxyl group containing elements in collagen, 2,4-dintro-N-(2-hydroxyethyl)-aniline (D-AN), having a molar absorbance in the order of $10^4$ mol/cm$^{-1}$*l$^{-1}$ at 340 nanometers (nm), and a shoulder at 415 nm, turning it bright yellow, and having the following structure, was chosen (due to its yellow color it allows one to follow ester formation, rinsing, and ester bond breaking with the naked eye).

Procedure

Two capped 40 ml polystyrene tubes, labeled as Tube A and Tube B, were each filled with 500 milligrams (mg) dry SEPHADEX CM-25 gel (Fluka), and suspended in 25 milliliters (ml) of an aqueous solution of 0.2 M MES (Aldrich, Belgium), pH=5.5.

To Tube A, a concentrated solution of D-AN (Sigma) in DMSO (50 mg/ml) was pipetted to reach a final concentration of 1 mg/ml, followed by the addition of 5 mg/ml N-hydroxysuccinimide. To Tube B the same reagents were added by the same procedure and under the same conditions. Then, to Tube B, 10 mg/ml water soluble carbodiimide (EDC, from Aldrich, Belgium) was added.

Tubes A and B were incubated on a shaker for 4 hours at room temperature. The tubes then were centrifuged at 1000 g and the supernatant carefully decanted. The treated SEPHADEX gel from each tube was then, shaken with 25 ml deoinized water for 5 minutes, followed by centrifugation at 1000 g and decantation. This procedure was repeated 3 times, followed by the same procedure with 1 M NaCl, and then repeated 5 more times with deionized water. After these rinsing steps the supernatant from each tube was colorless and showed no adsorption at 360 nm, indicating that all adsorbed D-AN was removed.

The SEPHADEX gel in Tube A, in which no carbodiimide was added to the buffer, was colorless, while the SEPHADEX gel in tube B had a yellow color, indicting that in the presence of carbodiimide, ester formation between the hydroxyl group of D-AN and the carboxyl groups in the gel had occurred. The gel was stored wet at 4° C. (wet for both tubes, wet here means that the gel was stored in its hydrated state, and not dried before storage).

Example 20

Hydrolysis of the Ester Bond in Phosphate Buffer

An aliquot of 650 mg of swollen substituted SEPHADEX gel from Tube B was added to a 10 ml polystyrene tube. Following this (at time t=0), 5 ml of a 0.1 M phosphate buffer, pH 7.4, composed of NaH$_2$PO$_4$ and Na$_2$HPO$_4$ (from Merck, Germany) was added (to the aliquot of SEPHADEX gel and put on a standard laboratory shaker) at 37° C.

At time t=30 minutes the polystyrene tube was centrifuged for 5 minutes at 1000 G and an aliquot of 300 microliters (µl) was taken from the supernatant, and stored in a freezer at 4° C. until analysis. The polystyrene tube containing the SEPHADEX gel was put back on the shaker and at time t=92 minutes, a second 300 µl aliquot of the supernatant was taken, as described above. At time t=190 minutes, a third 300 µl aliquot of the SEPHADEX gel was taken, centrifuged and stored as above.

At time t=1119 minutes, a fourth 300 µl aliquot of the SEPHADEX gel was taken, and processed as above.

Example 21

Hydrolysis of the Ester Bond in Carbonate Buffer

The procedure of Example 20 was followed, except that 5 ml of a 0.1 M carbonate buffer of pH=8.2, prepared from sodium bicarbonate (Aldrich, Belgium) was added to the aliquot of SEPHADEX gel in place of the phosphate buffer.

Example 22

Hydrolysis of the Ester Bond in Borate Buffer

The procedure of Example 20 was followed, except that of a 0.1 M borate buffer of pH=9.2, prepared from sodium borate (Aldrich, Belgium) was added to the aliquot of SEPHADEX gel in place of the phosphate buffer.

The stored samples were removed from the freezer, 280 µl of each sample was added to a well and the absorbance measured at 360 nm using a 96-well microplate reader (Spectra Max 190 from Molecular Devices, Sunnydale, Calif.). The results indicated that by increasing the pH, the rate of hydrolysis was increased. At pH=9.2, it was shown that nearly complete hydrolysis was achieved after 20 hours.

Figure 4:
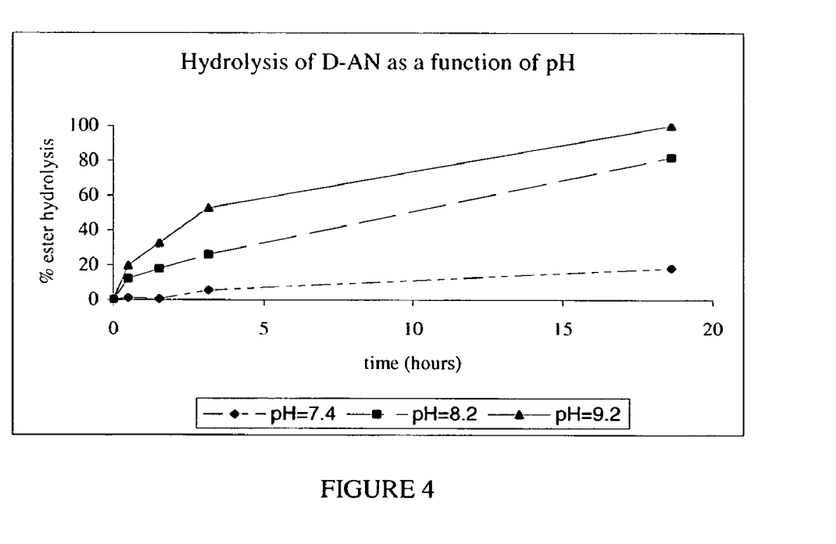
FIG. 4. Chart of the percentage of hydrolysis of the ester between D-AN and SEPHADEX CM gel at different pH's as a function of time at 37° C.

The percentage of hydrolysis as a function of time is depicted in FIG. 4. These results indicate that ester linkages can be formed by the action of carbodiimide in the presence of water, and that the esters formed can also be hydrolyzed using a buffer of pH>7.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for making a crosslinked material, the method comprising:
   providing a crosslinked material having zero-length ester crosslinks and spacer crosslinks, wherein the material included amine groups, carboxyl groups, and hydroxyl groups prior to crosslinking;
   removing at least a portion of the zero-length ester crosslinks from the crosslinked material.

2. The method of claim 1 wherein the crosslinked material is a crosslinked collagen-based material.

3. The method of claim 2 wherein the collagen-based material comprises whole tissue.

4. The method of claim 1 wherein at least 50% of the zero-length crosslinks are removed.

5. The method of claim 1 wherein removing at least a portion of the zero-length ester crosslinks comprises exposing the crosslinked material to hydrolyzing conditions.

6. The method of claim 5 wherein exposing the crosslinked material to hydrolyzing conditions comprises exposing the crosslinked material to an initial temperature of 4° C. to 40° C.

7. The method of claim 5 wherein exposing the crosslinked material to hydrolyzing conditions comprises exposing the crosslinked material to an initial pH of 2 to 11.

8. The method of claim 7 wherein exposing the crosslinked material to hydrolyzing conditions comprises exposing the crosslinked material to a buffered solution having a pH of 2 to 11.

9. The method of claim 5 wherein exposing the crosslinked material to hydrolyzing conditions comprises exposing the crosslinked material to an acidic buffered solution.

10. The method of claim 5 wherein exposing the crosslinked material to hydrolyzing conditions comprises exposing the crosslinked material to a basic buffered solution.

11. The method of claim 1 wherein removing at least a portion of the zero-length ester crosslinks comprises exposing the crosslinked material to an enzyme.

12. A method for crosslinking collagen-based material, the method comprising:
providing a collagen-based material having collagen amine groups, collagen carboxyl groups, and collagen hydroxyl groups;
blocking at least a portion of the collagen amine groups with a blocking agent to form blocked amine groups;
activating at least a portion of the collagen carboxyl groups after forming blocked amine groups to form activated carboxyl groups;
contacting the activated carboxyl groups with a polyfunctional spacer to crosslink the collagen-based material to form a crosslinked collagen-based material comprising spacer crosslinks and zero-length ester crosslinks; and
removing at least a portion of the zero-length ester crosslinks from the crosslinked collagen-based material.

13. The method of claim 12 wherein blocking at least a portion of the collagen amine groups with a blocking agent to form blocked amine groups comprises contacting at least a portion of the collagen amine groups with a blocking agent selected from the group consisting of an acylating agent, an aminating agent, a biologically active derivative thereof, and mixtures thereof.

14. The method of claim 12 wherein activating at least a portion of the collagen carboxyl groups to form activated carboxyl groups comprises contacting at least a portion of the collagen carboxyl groups with an activating agent selected from the group consisting of a carbodiimide, an azide, 1,1'-carbonyldiimidazole, N,N'-disuccinimidyl carbonate, 2-ethoxy-1-ethoxycarbonyl-1,2-dihydroquinoline, 1,2-benzisoxazol-3-yl-diphenyl phosphate, and N-ethyl-5-phenylisoxazolium-s'-sulfonate, and mixtures thereof.

15. The method of claim 14 wherein the activating agent is a carbodiimide.

16. The method of claim 12 wherein activating at least a portion of the collagen carboxyl groups to form activated carboxyl groups comprises contacting at least a portion of the collagen carboxyl groups with an activating agent in the presence of a stabilizing agent.

17. The method of claim 12 wherein the polyfunctional spacer is a diamine spacer.

18. The method of claim 12 wherein the collagen-based material comprises whole tissue.

19. The method of claim 12 wherein at least 50% of the zero-length crosslinks are removed.

20. The method of claim 12 wherein removing at least a portion of the zero-length ester crosslinks comprises exposing the crosslinked material to hydrolyzing conditions.

21. The method of claim 20 wherein exposing the crosslinked material to hydrolyzing conditions comprises exposing the crosslinked material to an initial temperature of 4° C. to 40° C.

22. The method of claim 20 wherein exposing the crosslinked material to hydrolyzing conditions comprises exposing the crosslinked material to an initial pH of 2 to 11.

23. The method of claim 20 wherein exposing the crosslinked material to hydrolyzing conditions comprises exposing the crosslinked material to a buffered solution having a pH of 2 to 11.

24. The method of claim 20 wherein exposing the crosslinked material to hydrolyzing conditions comprises exposing the crosslinked material to an acidic buffered solution.

25. The method of claim 20 wherein exposing the crosslinked material to hydrolyzing conditions comprises exposing the crosslinked material to a basic buffered solution.

26. The method of claim 12 wherein removing at least a portion of the zero-length ester crosslinks comprises, exposing the crosslinked material to an enzyme.

27. A method for crosslinking material, the method comprising:
providing a material having amine groups, carboxyl groups, and hydroxyl groups;
blocking at least a portion of the amine groups with a blocking agent to form blocked amine groups;
activating at least a portion of the carboxyl groups after forming blocked amine groups to form activated carboxyl groups;
contacting the activated carboxyl groups with a polyfunctional spacer to crosslink the material to form a crosslinked material comprising spacer crosslinks and zero-length ester crosslinks; and
removing at least a portion of the zero-length ester crosslinks from the crosslinked material.

28. The method of claim 27 wherein blocking at least a portion of the amine groups with a blocking agent to form blocked amine groups comprises contacting at least a portion of We amine groups with a blocking agent selected from the group consisting of an acylating agent, aminating agent, a biologically active derivative thereof, and mixtures thereof.

29. The method of claim 27 wherein activating at least a portion of the carboxyl groups to form activated carboxyl groups comprises contacting at least a portion of the carboxyl groups with an activating agent selected from the group consisting of a carbodiimide, an azide, 1,1'-carbonyldiimidazole, N,N'-disuccinimidyl carbonate, 2-ethoxy-1-ethoxycarbonyl-1,2-dihydroquinoline, 1,2-benzisoxazol-3-yl-diphenyl phosphate, and N-ethyl-5-phenylisoxazolium-s'-sulfonate and mixtures thereof.

30. The method of claim 27 wherein activating at least a portion of the carboxyl groups to form activated carboxyl groups comprises contacting at least a portion of the carboxyl groups with an activating agent in the presence of a stabilizing agent.

31. The method of claim 27 wherein the polyfunctional spacer is a diamine spacer.

32. The method of claim 27 wherein removing at least a portion of the zero-length ester crosslinks comprises exposing the crosslinked material to hydrolyzing conditions.

33. The method of claim 32 wherein exposing the crosslinked material to hydrolyzing conditions comprises exposing the crosslinked material to an initial temperature of 4° C. to 40° C. and an initial pH of 2 to 11.

34. The method of claim 32 wherein exposing the crosslinked material to hydrolyzing conditions comprises exposing the crosslinked material to an acidic buffered solution.

35. The method of claim 32 wherein exposing the crosslinked material to hydrolyzing conditions comprises exposing the crosslinked material to a basic buffered solution.

36. The method of claim 27 wherein removing at least a portion of the zero-length ester crosslinks comprises exposing the crosslinked material to an enzyme.

37. A method for making a bioprosthetic device, the method comprising:
providing a crosslinked collagen-based material having zero-length ester crosslinks and spacer crosslinks, wherein the collagen-based material included collagen amine groups, collagen carboxyl groups, and collagen hydroxyl groups prior to crosslinking; and
removing at least a portion of the zero-length ester crosslinks from the crosslinked collagen-based material.

38. The method of claim 37 wherein the bioprosthetic device is a heart valve.

39. The method of claim 37 wherein the collagen-based material comprises whole tissue.

40. The method of claim 37 wherein at least 50% of the zero-length ester crosslinks are removed.

41. The method of claim 37 wherein removing at least a portion of the zero-length ester crosslinks comprises exposing the collagen-based crosslinked material to hydrolyzing conditions.

42. The method of claim 41 wherein exposing the crosslinked collagen-based material to hydrolyzing conditions comprises exposing the crosslinked collagen-based material to an initial temperature of 4° C. to 40° C.

43. The method of claim 41 wherein exposing the crosslinked collagen-based material to hydrolyzing conditions comprises exposing the crosslinked collagen-based material to an initial pH of 2 to 11.

44. The method of claim 41 wherein exposing the crosslinked collagen-based material to hydrolyzing conditions comprises exposing the crosslinked collagen-based material to a buffered solution having a pH of 2 to 11.

45. The method of claim 41 wherein exposing the crosslinked collagen-based material to hydrolyzing conditions comprises exposing the crosslinked collagen-based material to an acidic buffered solution.

46. The method of claim 41 wherein exposing the crosslinked collagen-based material to hydrolyzing conditions comprises exposing the crosslinked collagen-based material to a basic buffered solution.

47. The method of claim 37 wherein removing at least a portion of the zero-length ester crosslinks comprises exposing the crosslinked collagen-based material to an enzyme.

48. A method for making a bioprosthetic device, the method comprising:
providing a collagen-based material having collagen amine groups, collagen carboxyl groups, and collagen hydroxyl groups;
blocking at least a portion of the collagen amine groups with a blocking agent to form blocked amine groups;
activating at least a portion of the collagen carboxyl groups after forming blocked amine groups and blocked hydroxyl groups to form activated carboxyl groups;
contacting the activated carboxyl groups with a polyfunctional spacer to crosslink the collagen-based material to form a crosslinked collagen-based material comprising spacer crosslinks and zero-length ester crosslinks; and
removing at least a portion of the zero-length ester crosslinks from the crosslinked material.

49. The method of claim 48 wherein the collagen-based material comprises whole tissue.

50. The method of claim 48 wherein blocking at least a portion of the amine groups with a blocking agent to form blocked amine groups comprises contacting at least a portion of the amine groups with a blocking agent selected from the group consisting of an acylating agent, an aminating agent, a biologically active derivative thereof, and mixtures thereof.

51. The method of claim 48 wherein activating at least a portion of the carboxyl groups to form activated carboxyl groups comprises contacting at least a portion of the carboxyl groups with an activating agent selected from the group consisting of a carbodiimide, an azide, 1,1'-carbonyldiimidazole, N,N'-disuccinimidyl carbonate, 2-ethoxy-1-ethoxycarbonyl-1,2-dihydroquinoline, 1,2-benzisoxazol-3-yl-diphenyl phosphate, and N-ethyl-5-phenylisoxazolium-s'-sulfonate and mixtures thereof.

52. The method of claim 48 wherein activating at least a portion of the carboxyl groups to form activated carboxyl groups comprises contacting at least a portion of the carboxyl groups with an activating agent in the presence of a stabilizing agent.

53. The method of claim 48 wherein the polyfunctional spacer is a diamine spacer.

54. The method of claim 48 wherein removing at least a portion of the zero-length ester crosslinks comprises exposing the crosslinked material to hydrolyzing conditions.

55. The method of claim 54 wherein exposing the crosslinked material to hydrolyzing conditions comprises exposing the crosslinked material to an initial temperature of 4° C. to 40° C. and an initial pH of 2 to 11.

56. The method of claim 54 wherein exposing the crosslinked material to hydrolyzing conditions comprises exposing the crosslinked material to an acidic buffered solution.

57. The method of claim 54 wherein exposing the crosslinked material to hydrolyzing conditions comprises exposing the crosslinked material to a basic buffered solution.

58. The method of claim 48 wherein removing at least a portion of the zero-length ester crosslinks comprises exposing the crosslinked material to an enzyme.

59. A bioprosthetic device preparable by the method of claim 37.

60. A bioprosthetic device preparable by the method of claim 48.

* * * * *

UNITED STATES PATENT AND TRADEMARK OFFICE
CERTIFICATE OF CORRECTION

| | | |
|---|---|---|
| PATENT NO. | : 7,053,051 B2 | Page 1 of 1 |
| APPLICATION NO. | : 10/974206 | |
| DATED | : May 30, 2006 | |
| INVENTOR(S) | : Hendriks et al. | |

It is certified that error appears in the above-identified patent and that said Letters Patent is hereby corrected as shown below:

On the Title page, item (75), inventor Marc Hendriks' address, please delete "Brunssum" and replace with --Brussum--.

Column 22, line 46, please delete "We" and replace with --the--.

Signed and Sealed this

Fourteenth Day of November, 2006

JON W. DUDAS
*Director of the United States Patent and Trademark Office*